United States Patent
Prause et al.

(10) Patent No.: US 10,488,367 B2
(45) Date of Patent: *Nov. 26, 2019

(54) ULTRASONIC-PULSE-ECHO FLAW INSPECTION AT A HIGH TESTING SPEED ON THIN-WALLED PIPES IN PARTICULAR

(71) Applicant: GE Sensing & Inspection Technologies GmbH, Hurth (DE)

(72) Inventors: Reinhard Prause, Sankt Augustin (DE); Wolfgang Dick, Hurth (DE)

(73) Assignee: GE Sensing & Inspection Technologies GmbH, Hurth (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/274,708

(22) Filed: Feb. 13, 2019

(65) Prior Publication Data

US 2019/0178846 A1 Jun. 13, 2019

Related U.S. Application Data

(63) Continuation of application No. 15/124,702, filed as application No. PCT/EP2015/054982 on Mar. 10, 2015, now Pat. No. 10,241,084.

(30) Foreign Application Priority Data

Mar. 10, 2014 (DE) .......................... 10 2014 103 165
Jul. 11, 2014 (DE) .......................... 10 2014 109 793

(51) Int. Cl.
*G01N 29/11* (2006.01)
*G01N 29/22* (2006.01)
(Continued)

(52) U.S. Cl.
CPC ........... *G01N 29/043* (2013.01); *G01N 29/11* (2013.01); *G01N 29/221* (2013.01);
(Continued)

(58) Field of Classification Search
CPC .. G01N 29/11; G01N 29/221; G01N 29/2487; G01N 29/36; G01N 29/043;
(Continued)

(56) References Cited

U.S. PATENT DOCUMENTS

| 3,646,805 A | 3/1972 | Walters |
| 3,724,262 A | 4/1973 | Niklas |

(Continued)

FOREIGN PATENT DOCUMENTS

| CA | 1338766 C | 12/1996 |
| DE | 1960458 A1 | 6/1971 |

(Continued)

OTHER PUBLICATIONS

German Search Report issued in connection with corresponding DE Application No. 102014103165.2 dated Jul. 11, 2014.
(Continued)

*Primary Examiner* — Jacques M Saint Surin
(74) *Attorney, Agent, or Firm* — Mintz Levin Cohn Ferris Glovsky and Popeo, P.C.

(57) ABSTRACT

Embodiments relate to a method for ultrasonic testing according to the pulse-echo method as well as an arrangement for performing such a method. By means of an ultrasonic transducer, an ultrasonic pulse is obliquely incident into a sound incidence surface of a test object. Next, an echo signal is received from the test object. This takes place either by means of the ultrasonic transducer, which has emitted the ultrasonic pulse or with another ultrasonic transducer. The time amplitude characteristic of the echo signal is evaluated in a predefined defect expectation interval of time. The evaluation step includes, in at least one section of the amplitude characteristic, an amplification of the amplitude and/or a reduction in the threshold value. For
(Continued)

example, the amplitude of the received echo signal is then compared with the predefined threshold value.

20 Claims, 3 Drawing Sheets

(51) Int. Cl.
    *G01N 29/24*      (2006.01)
    *G01N 29/36*      (2006.01)
    *G01N 29/38*      (2006.01)
    *G01N 29/40*      (2006.01)
    *G01N 29/44*      (2006.01)
    *G01N 29/04*      (2006.01)

(52) U.S. Cl.
    CPC ......... *G01N 29/2487* (2013.01); *G01N 29/36* (2013.01); *G01N 29/38* (2013.01); *G01N 29/40* (2013.01); *G01N 29/4463* (2013.01); *G01N 2291/044* (2013.01); *G01N 2291/056* (2013.01)

(58) Field of Classification Search
    CPC .... G01N 29/40; G01N 29/4463; G01N 29/38; G01N 2291/044; G01N 2291/056
    USPC .......................................................... 73/579
    See application file for complete search history.

(56) References Cited

U.S. PATENT DOCUMENTS

| | | | |
|---|---|---|---|
| 3,895,685 A | 7/1975 | Gillette et al. | |
| 3,942,358 A | 3/1976 | Pies | |
| 4,068,524 A | 1/1978 | Lewis et al. | |
| 4,513,621 A | 4/1985 | Renzel et al. | |
| 5,349,860 A | 9/1994 | Nakano et al. | |
| 5,431,054 A | 7/1995 | Reeves et al. | |
| 5,454,045 A | 9/1995 | Perkins et al. | |
| 5,497,662 A | 3/1996 | Dykes | |
| 5,554,808 A | 9/1996 | Chiao | |
| 8,857,262 B2 * | 10/2014 | Turner | B61K 9/10 |
| | | | 73/597 |
| 9,921,186 B2 * | 3/2018 | Lingenberg | G01N 23/18 |
| 10,139,373 B2 * | 11/2018 | Chinta | G01N 29/043 |
| 10,241,084 B2 * | 3/2019 | Prause | G01N 29/11 |
| 2004/0035208 A1 | 2/2004 | Diaz et al. | |
| 2006/0016263 A1 | 1/2006 | Kleinert | |
| 2006/0219011 A1 | 10/2006 | Siddu et al. | |
| 2014/0123761 A1 * | 5/2014 | Turner | G01N 29/11 |
| | | | 73/628 |
| 2015/0049580 A1 | 2/2015 | Skoglund et al. | |

FOREIGN PATENT DOCUMENTS

| | | |
|---|---|---|
| DE | 2621223 A1 | 12/1976 |
| DE | 3307224 C1 | 7/1984 |
| DE | 3822699 A1 | 1/1990 |
| DE | 202013105253 U1 | 2/2014 |
| EP | 2249152 A2 | 11/2010 |
| WO | 2004005913 A1 | 1/2004 |

OTHER PUBLICATIONS

PCT Search Report and Written Opinion issued in connection with corresponding PCT Application No. PCT/EP2015/054982 dated Jun. 22, 2015.

* cited by examiner

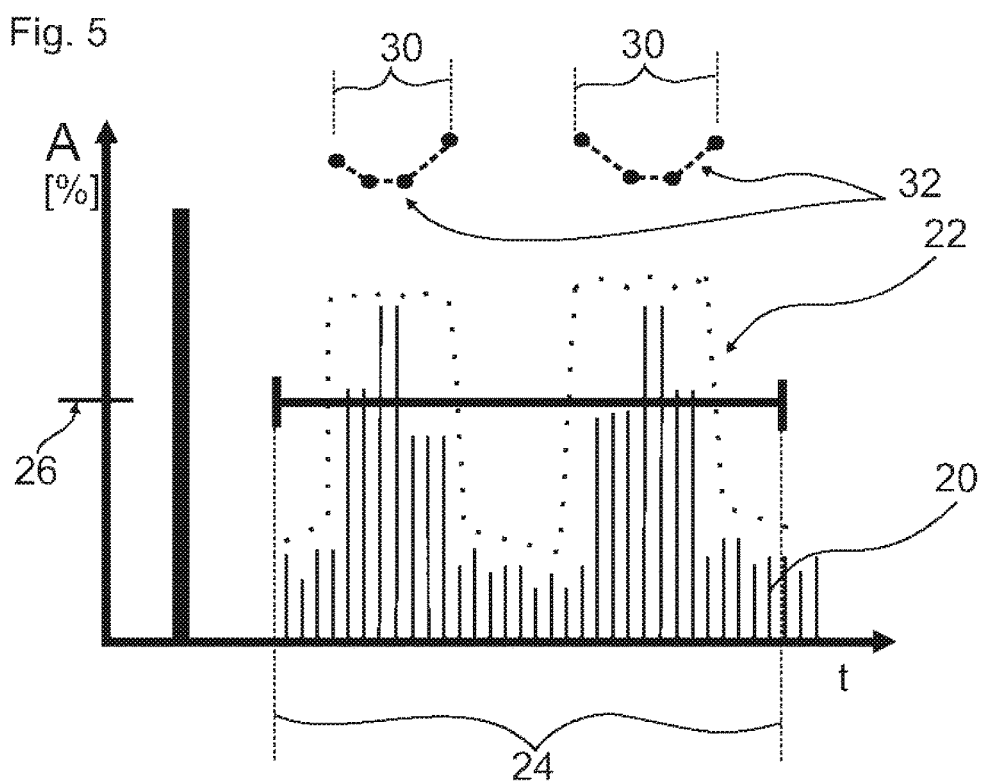

ULTRASONIC-PULSE-ECHO FLAW INSPECTION AT A HIGH TESTING SPEED ON THIN-WALLED PIPES IN PARTICULAR

CROSS-REFERENCE TO RELATED APPLICATION

This application is a continuation of U.S. patent application Ser. No. 15/124,702 entitled "ULTRASONIC-PULSE-ECHO FLAW INSPECTION AT A HIGH TESTING SPEED ON THIN-WALLED PIPES IN PARTICULAR," filed Sep. 9, 2016, which is a national stage entry of Application No. PCT/EP2015/054982 entitled "ULTRASONIC-PULSE-ECHO FLAW INSPECTION AT A HIGH TESTING SPEED ON THIN-WALLED PIPES IN PARTICULAR," filed on Mar. 10, 2015, which are hereby incorporated herein by reference in their entireties.

BACKGROUND

The testing speed of ultrasonic test objects with an oblique angle of sound incidence in pulse-echo technology is linked to the sound field expansion across the direction of sound propagation of the ultrasonic field emitted by the ultrasonic transducer. Thus, in ultrasonic testing of thin-walled pipes, in which the pipe is "monitored" in the axial direction for suspicious reflections due to flaws in the pipe caused by multiple reflections on the walls of the pipe due to translational and/or rotational relative movements, for example, due a relative spiral movement, between the ultrasonic transducer and the pipe (i.e. test object). The "lower" it is possible to identify defect echoes in the material of the test object or in thin-walled test objects in the case of oblique incidence of sound, despite acoustic damping, the greater the distance away from the point of sound incidence, the faster the complete detection of the test object can be.

Due to the use of acoustic transducers having a greater sound-emitting (i.e. acoustically active) area, there is the possibility of mechanically enlarging the sound field expansion. However, this procedure may cause the device to become expensive and also the requirements of acoustic coupling between the test object and the ultrasonic transducer becomes higher. However, a greater sound field expansion permits more rapid testing of a workpiece due to possible cost savings.

There is therefore a demand for a method for ultrasonic testing according to the pulse-echo method, in which detection of defects is improved and, in particular, in which complete detection of the test object can be carried out more rapidly.

BRIEF DESCRIPTION

It should be pointed out that the features and steps of the method, which are discussed individually, may be combined with one another in any technically logical manner and may demonstrate additional embodiments. The description additionally characterizes and specifies the embodiments in conjunction with the figures in particular.

The method according to an embodiment for ultrasonic testing according to the pulse-echo method has a step of oblique incidence of an ultrasonic pulse into a test object via a sound incidence surface by using an ultrasonic transducer. "Oblique" in the sense of the application means that the main direction of propagation of the sound emitted from the ultrasonic transducer forms a non-right angle with the sound incidence surface, for example, an angle of 17°, and thus the sound has a propagation component in the test object that is perpendicular to the plumb line to the input surface. The angle of incidence set in the step of oblique sound incidence is selected so that the main direction of propagation of the ultrasonic pulse assumes an angle to the sound incidence surface in the range of 40° to 50°, for example, approximately or exactly 45.0°, immediately after passing through the input surface.

According to an embodiment, a step of receiving the echo signal from the test object with the ultrasonic transducer already functioning as a transmitter or another receiving ultrasonic transducer is. The transmission and reception take place through the same ultrasonic transducer. In addition to conventional test heads having round, rectangular or square ultrasonic transducers in various model sizes, for example, phased array test heads may also be used.

Furthermore, according to an embodiment, an evaluation of the amplitude characteristic of the echo signal over time in a predefined defect expectation interval of time is provided. The step of evaluation includes, for example, comparison of the amplitude with a predefined threshold value to detect a defect in the test object, for example, when the threshold value is exceeded. The step of evaluation includes, according to an embodiment, amplification, for example, electronic amplification in at least one section of the amplitude characteristic of the echo signal in the defect expectation interval of time. Amplification in the sense of the application means, for example, amplifying the echo signal by a fixed gain factor in the respective section. Additionally or alternatively, a decline in the threshold value may occur in the section of the amplitude characteristic of the echo signal. According to an embodiment, this amplification of the amplitude echo is to be equated with the reduction in the threshold value over time for defect detection and is thus also covered by the idea.

In comparison with known methods, the probability of detection of defects can be improved by the method according to the embodiments in the space of the test object through which the ultrasonic field passes, in particular, a larger volume and/or a larger surface area being detectable per echo emission at the same ultrasonic emission power because the defect expectation interval of time can be increased in particular.

According to an embodiment of the method, the gain factor is varied in one section. The gain factor is varied in one section, in which a received echo signal has a pronounced jump behavior. The gain factor for the amplitudes of the received echo signals is increased immediately before and after the echo signal having the pronounced jump behavior.

According to another embodiment of the method, the gain factor in the at least one section of the amplitude characteristic of the echo signal in the defect expectation interval of time increases steadily over time or decreases steadily over time. In particular the echo signal is subject to a damping over time, which can be attributed to a prolonged transit time, for example, due to reflections of an ultrasonic pulse in the test object. In general terms, it can be stated that the longer an ultrasonic pulse is underway in a test object and the more often it is reflected, the greater is the damping, wherein the term "longer" in the sense of the application is to be understood as longer in time and also as longer in space. If an ultrasonic pulse is underway in a test object for a longer period of time, then it usually also travels a greater distance in the test object. Consequently, the received echo signal becomes progressively weaker within a defect expectation interval of time. A decline in the amplitude characteristic of the echo signal over time, the decline being induced in this way, can be compensated by an increase in the gain factor in the defect expectation interval of time.

In particular, in one embodiment of the method, the drop in amplitude, which is attributed to the damping due to the material and the geometry of the test object, is compensated. This is the case in particular when the echoes to be compared originate from a sound field at a comparatively great distance, which is formed due to multiple reflections and is therefore diffuse. For example, this occurs with a thin-walled pipe or sheet metal after a plurality of reflections on the wall (jumps) or when the ultrasonic receiver has large dimensions relative to the thickness of the material.

Amplitudes of echoes from a diffuse sound field at a comparatively great distance may surprisingly also be used for defect analysis through the procedure. In such an embodiment, the section of the amplification of the amplitude characteristic is located at the back end, chronologically, of the defect expectation interval of time. Due to this amplification of and/or reduction in the threshold value, the sensitivity is increased, so that with a longer transit time of the echo signal, the amplitude damping can be counteracted and thus echoes that have run for a longer period of time in the test object can be used for the defect analysis.

In another embodiment, the decline in amplitude, which is caused by a power loss at the side in the sound emission cone of the ultrasonic transducer, is compensated. Thus even defects which lie in the region of the decline in the sound emission cone at the side and whose amplitude drop is caused by this drop in the sound emission cone at the side can also be detected as flaws.

In another embodiment, multiple sections of the amplitude characteristic of the echo signal are provided in the defect expectation interval of time, wherein the sections in the time characteristic of the gain factor are different. For example, in an early first section of the defect expectation interval of time, the decline in amplitude, which is caused by the power loss of the sound emission cone for early returning echoes, is compensated in an early first section of the defect expectation interval of time, and in a late second section of the defect expectation interval of time, the damping of echoes from the diffuse sound field at a great distance is compensated, so that the amplitudes of these echoes are amplified at least, so that they exceed the threshold value. The method is designed so that the gain factor increases steadily over the entire amplitude characteristic of the echo signal in the defect expectation interval of time.

The test object is a body having parallel walls, wherein one wall includes the sound incidence surface. In an embodiment, the body is a sheet metal or a pipe. The method according to an embodiment is suitable for detecting both transverse defects as well as longitudinal defects on the walls. The method is suitable in particular for detection of transverse defects in thin-walled pipes, i.e., defects whose extent is essentially across the longitudinal extent of the pipe.

The test object is at a distance from the walls (i.e. wall thickness) in the range of 0.5 mm to 10.0 mm, although it may be beneficial to be in the range of 1.0 mm to 8.0 mm, and even more beneficial in the range of 1.5 mm to 4.0 mm.

The ultrasonic transducer has a maximum outside dimension of its sound-emitting surface, which is in the range of greater than 10.0 mm, although it may be beneficial to be greater than or equal to 12.0 mm, such as 18.0 mm or 24.0 mm.

In an embodiment, the duration of the defect expectation interval of time is selected so that multiple reflections in the test object are detected by the time characteristic of the echo signal in the defect expectation interval of time. Additionally, the defect expectation interval of time is selected so that multiple reflections on the walls of the test object (internal reflections) are detected by the time characteristic of the echo signal.

In another embodiment, the method may have multiple sound incidence steps following one another in time and multiple intermediate or simultaneous steps of relative movement to achieve the most thorough possible sound bombardment of the test object. For example, the test object is rotated about one axis in the steps of the relative movement, and the ultrasonic transducer executes a translational movement along the sound incidence surface of the test objects, thus resulting in a spiral-shaped relative movement.

Embodiments also relate to an arrangement for ultrasonic testing according to the pulse-echo method, which has an ultrasonic transducer for oblique sound incidence of an ultrasonic pulse over a sound incidence surface into a test object and for receiving the echo signal from the test object and an evaluation unit for evaluation of the amplitude characteristic of the echo signal over time in a predefined defect expectation interval of time and for comparison of the amplitude with a predefined threshold value. The evaluation unit is also designed according to the embodiments to amplify the amplitude characteristic of the echo signal in at least one section of the defect expectation interval of time and/or to lower the threshold. The change may be continuous or abrupt.

The arrangement includes a body having parallel walls as the test object, wherein one wall includes the sound incidence surface. The body may be a pipe or a sheet metal.

Essential features of one embodiment, in particular for testing thin-walled pipes, can be summarized as follows:

The testing speed in transverse defect testing depends on the material to be tested due to the effective sound field expansion, among other things. The electronic increase in the sound field expansion and thus the increase in testing speed are important aspects of the embodiments.

The amplitudes of defect signals depend on the transit times and/or the reflections, multiple reflections and/or discontinuities in the wall. The effective widths of the sound field resulting from the decline in sensitivity (based on −x dB) determine two important factors: the testing speed and the reproducibility. This is true in particular of transverse defect testing in pipes.

Based on the ultrasonic transducer size and the thickness of the pipe wall to be tested, there is no pronounced jump behavior for the defect indication of the inside wall and the outside wall with thin-walled pipes, i.e., the defect indication is reduced continuously with the distance from the ultrasonic test head.

This can be compensated by lengthening the defect expectation interval of time accordingly and a programmable sensitivity equalization/an increase in gain is carried out over the length/transit time of the evaluation aperture (DAC).

If the signal-to-noise ratio is high enough, this equalization may take place for any length of time. Due to the sensitivity correction as a function of the path traveled, the evaluation is possible not only in the first jump but also in subsequent jumps. This results in a significant improvement in the effective width of the sound field and thus also an increase in the testing speed.

BRIEF DESCRIPTION OF THE DRAWINGS

With reference to the figures, additional features of the embodiments will be explained and illustrated below in a manner to be understood without restriction. These drawings show schematically:

FIG. 5: a diagram of the amplitudes of the received echo signals in an interval of time with some definite jump behavior of the echo signals.

In the different figures, parts that are equivalent with regard to their function are always labeled with the same reference numerals, so that they are usually described only once.

It should be emphasized here again that the figures are purely schematic diagrams, which do not claim to be drawn true to scale.

DETAILED DESCRIPTION

Figure 1:
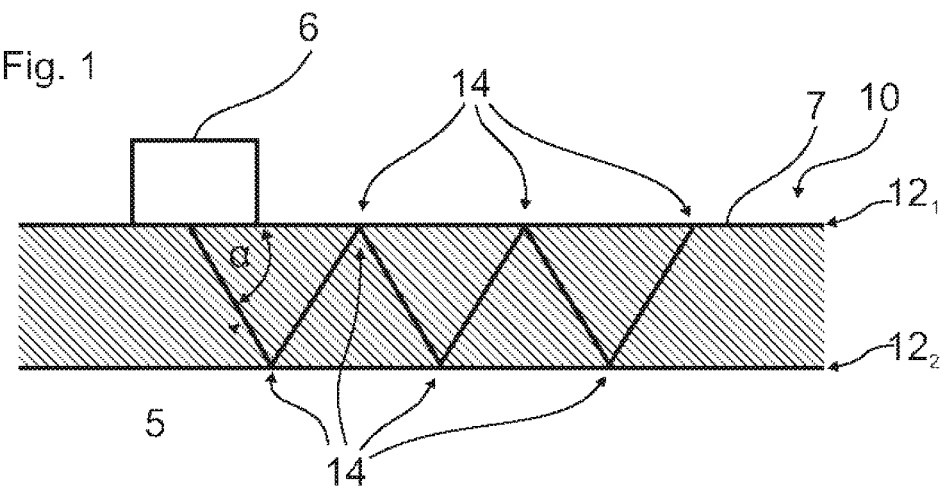
FIG. 1: a diagram of the oblique sound incidence of an ultrasonic pulse into a test object and multiple reflections within the test object.

FIG. 1 shows schematically how an ultrasonic pulse 5 has oblique incidence into a test object 10 over a sound incidence surface 7 by using an ultrasonic transducer 6. The sound incidence angle, which is set within the ultrasonic transducer 6, is selected so that, immediately after passage through the sound incidence surface 7, the main direction of propagation of the ultrasonic pulse 5 forms an angle α of approximately 45° to the sound incidence surface. In the exemplary embodiment shown here, it is a test object 10 having parallel walls 12, for example, a pipe or sheet metal. One of the walls 12 is the outside wall $12_1$ of the test object and the other wall 12 is the inside wall $12_2$ of the test object. The outside wall $12_1$ includes the sound incidence surface 7 of the ultrasonic pulse 5. Reflections 14 of the ultrasonic pulse 5 on the walls 12 of the test object 10 are shown, wherein the ultrasonic pulse 5 is reflected several times on the walls 12 within the test object 10.

Figure 2A:
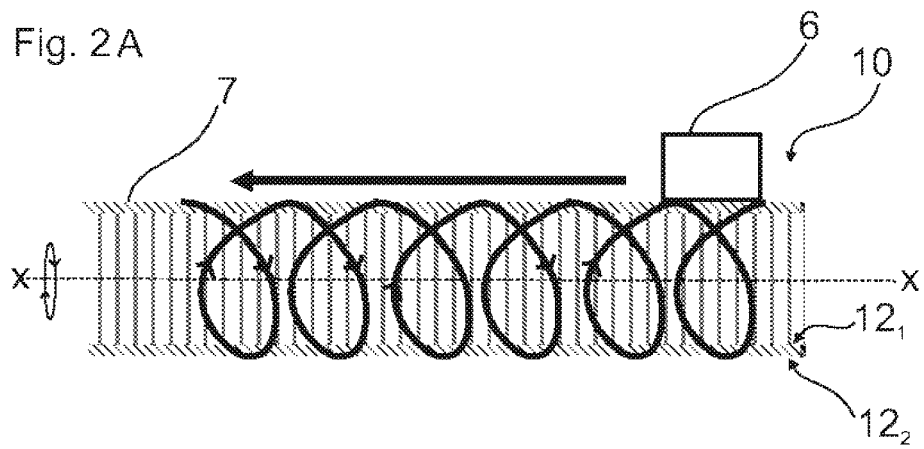
FIG. 2A: a diagram of a rotational and translational relative movement between an ultrasonic transducer and a test object.
Figure 2B:
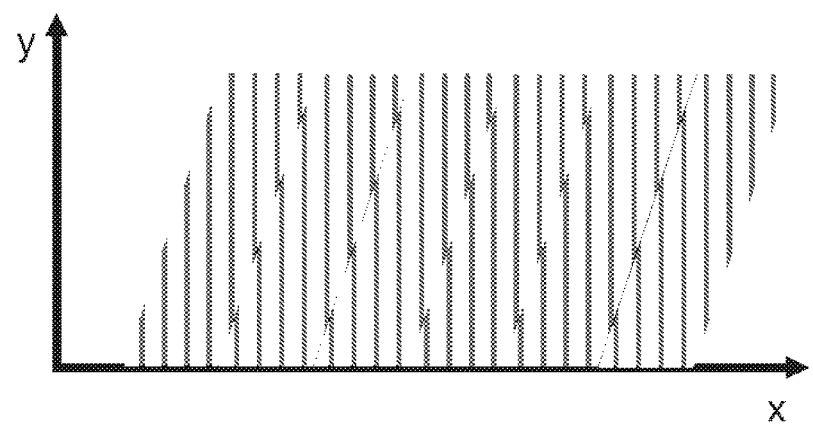
FIG. 2B: a projection of a surface tested in multiple rotations of the test object.

FIG. 2A shows schematically a diagram of a relative rotational movement and a relative translational movement between an ultrasonic transducer 6 and a test object 10. The test object 10 is a pipe, which forms an outside wall $12_1$ and an inside wall $12_2$, which are parallel to one another. The pipe can be rotated about an axis x-x, which forms the central axis of the pipe at the same time. During an ultrasonic test, the ultrasonic transducer 6 is arranged on the outside wall $12_1$ of the test object 10, which at the same time forms the sound incidence surface 7 by means of which the ultrasonic pulse 5 is input into the test object 10. The sound incidence of the ultrasonic pulses 5 takes place in a plurality of sound incidence steps following one another chronologically. Intermediately or simultaneously with the sound incidence, the ultrasonic transducer 6 is moved along the sound incidence surface 7 in the direction of the axis x-x and the test object 10 is rotated about the axis x-x. This yields a relative spiral movement between the ultrasonic transducer 6 and the test object 10. FIG. 2B shows schematically the projections of the surfaces tested per revolution of the test object 10.

Figure 3:
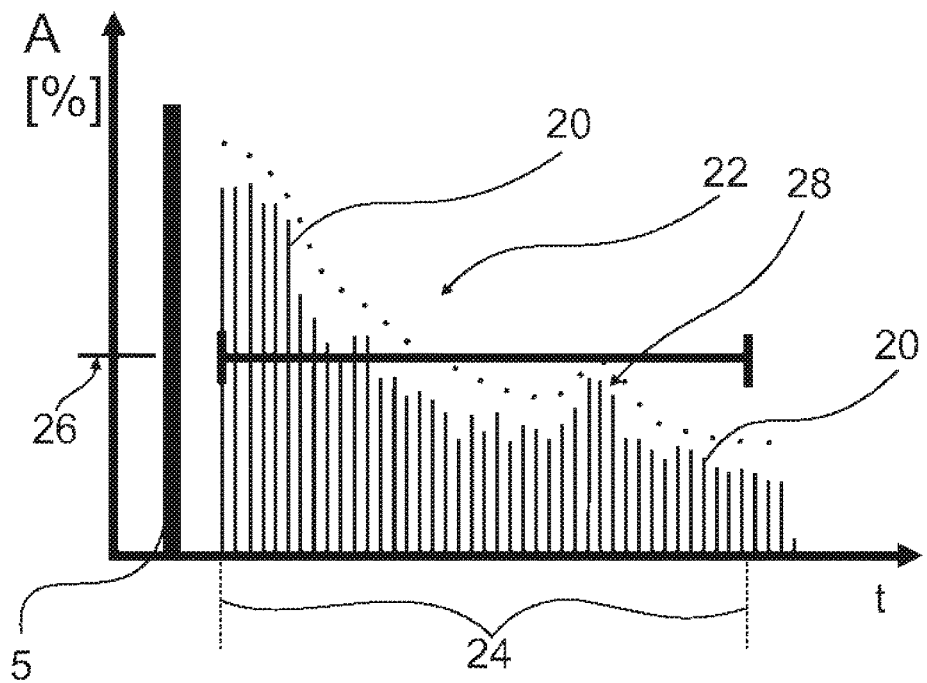
FIG. 3: a diagram of the amplitudes of the received echo signals in an interval of time without an evaluation step.

FIG. 3 shows schematically the echo signals 20 received from a test object 10 over time t. An echo signal 20 is depicted as a bar having an amplitude A. As a reference, the ultrasonic pulse 5 incidence is represented schematically with the amplitude A. In addition, the essential amplitude characteristic 22 is diagrammed as the envelope around the echo signals 20. The amplitude A of the echo signals 20 is compared with a threshold value 26 within a defect expectation interval of time 24. If this threshold value 26 is exceeded, a defect 28 in the test object 10 is detected. In the example shown here, the amplitude A of the echo signals 20 declines continuously over the time t, and this decline is to be attributed to damping due to the material and the geometry of the test object 10, for example. It may happen that defects 28 are not detected because the amplitudes A of the respective echo signals 20 are below the threshold value 26 because of this damping.

Figure 4:
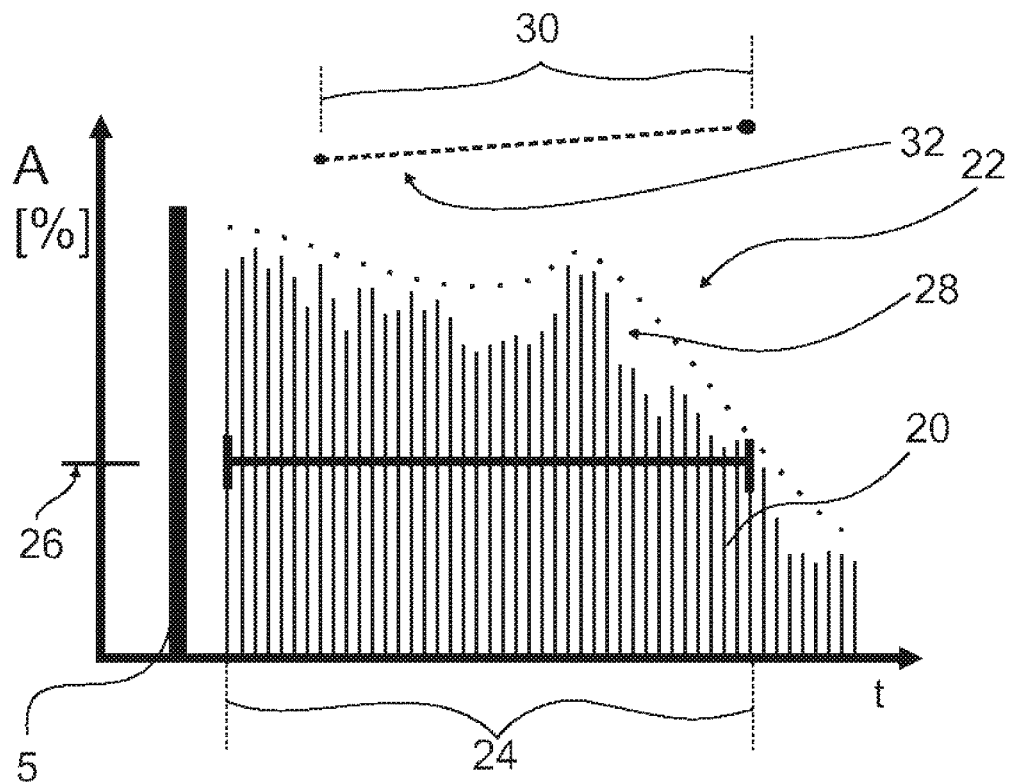
FIG. 4: a diagram of the amplitudes of the received echo signals in an interval of time with a gain step.

FIG. 4 shows schematically the echo signals 20 received from a test object 10 over time t. As is already known from FIG. 3, a single echo signal 20 is depicted as a bar having the amplitude A. The amplitudes A of the echo signals 20 are compared with the threshold value 26 within the defect expectation interval of time 24, wherein the amplitudes A of the echo signals 20 are amplified in at least one section 30 of the defect expectation interval of time 24. The curve of the gain factor 32 is also shown. The gain factor 32 increases within the section 30 and over the entire defect expectation interval 24. Due to the step of amplification of the echo signals 20, the defect 28 is now also identified, its amplitudes A without this step, as shown in FIG. 1, being below the threshold value 26. The amplitude characteristic 22 is depicted as an envelope around the echo signals 20, as is found after the step of evaluation and amplification of the amplitudes A.

FIG. 5 shows schematically the echo signals 20 received from a test object 10 over a time t. A single echo signal 20 is depicted as a bar having an amplitude A, and the incident ultrasonic pulse 5 with its amplitude A is diagrammed as a reference. This also shows the amplitude characteristic 22 as the envelope around the echo signals 20 after the step of evaluation and amplification of their amplitudes A within the defect expectation interval of time 24. Within the defect expectation interval of time 24, a definite jump behavior of the echo signals 20 is shown twice. Within the sections 30 in which this jump behavior occurs, the gain factor 32 is varied for the evaluation. The variation in the gain factor 32 is depicted schematically. Thus, gain factor 32, within the respective sections 30, before and after the echo signals 20, shows the jump behavior as higher.

It is to be understood that even though numerous characteristics and advantages of various embodiments have been set forth in the foregoing description, together with details of the structure and functions of various embodiments, this disclosure is illustrative only, and changes may be made in detail, especially in matters of structure and arrangement of parts within the principles of the embodiments to the full extent indicated by the broad general meaning of the terms in which the appended claims are expressed. It will be appreciated by those skilled in the art that the teachings disclosed herein can be applied to other systems without departing from the scope and spirit of the application.

The invention claimed is:

1. A method for ultrasonic testing, comprising:
using a phased array ultrasonic transducer including a first ultrasonic transducer element and a second ultrasonic transducer element to cause oblique sound incidence of an ultrasonic pulse transmitted via an input surface into a test object, the ultrasonic pulse transmitted by the first ultrasonic transducer element;
receiving the echo signal from the test object by the second ultrasonic transducer element; and
evaluating the amplitude characteristic of the echo signal over time in a predefined defect expectation interval of time for comparison of the amplitude with a predefined threshold value,
wherein the step of evaluation includes amplification of the amplitude with at least one of a gain factor and a reduction in the threshold value in at least one section of the amplitude characteristic of the echo signal in the defect expectation interval of time.

2. The method according to claim 1, wherein the gain factor varies within the at least one section.

3. The method according to claim 1, wherein the amplification of the amplitude or the reduction in the threshold value in the at least one section is designed so that a drop in amplitude, which is brought about by damping, is due to at least one of the damping and a power loss and is compensated partially.

4. The method according to claim 3, wherein the damping is attributed to at least one of the material and the geometry of the test object and by a power loss at the side of the sound emission cone of the ultrasonic transducer.

5. The method according to claim 1, wherein the at least one section is situated on the back end chronologically of the defect expectation interval of time.

6. The method according to claim 1, wherein the gain factor in the at least one section of the amplitude characteristic of the echo signal in the defect expectation interval of time increases steadily with time or decreases steadily with time.

7. The method according to claim 1, wherein the amplitude characteristic of the echo signal comprises a plurality of sections in the defect expectation interval of time, wherein the sections differ in at least one of the characteristic of the gain factor over time and in the threshold value variation.

8. The method according to claim 7, wherein the gain factor increases steadily over the entire amplitude characteristic of the echo signal in the defect expectation interval of time.

9. The method according to claim 1, wherein the test object is a body having walls parallel to one another, and one of the walls comprises the sound incidence surface.

10. The method according to claim 9, wherein the test object has a wall thickness in the range of 0.5 mm to 10.0 mm.

11. The method according to claim 9, wherein the body is comprised of a pipe or a sheet metal.

12. The method according to claim 1, wherein the duration of the defection expectation interval of time is selected, so that multiple reflections in the test object are covered by the time characteristic of the echo signal in the defect expectation interval of time.

13. The method according to claim 12, wherein the multiple reflections of the walls of the test object are covered by the time characteristic of the echo signal in the defect expectation interval of time.

14. The method according to claim 1, having a plurality of sound incidence steps following one another in time and a plurality of intermediate or simultaneous steps of relative movement.

15. The method according to claim 14, wherein the relative movement comprises at least one of relative rotational and translational movement, between the ultrasonic transducer emitting the sound and the test object, to achieve a complete sound bombardment of the test object.

16. The method according to claim 1, wherein the sound incidence angle set in the step of oblique sound incidence is selected so that the main direction of propagation of the ultrasonic pulse forms an angle with the sound incidence surface immediately after the ultrasonic pulse passes through the sound incidence surface, this angle being in the range of 40° to 50°.

17. The method according to claim 1, wherein the ultrasonic transducer has a maximum outside dimension of its sound-emitting surface in the range of greater than 10.0 mm.

18. The method according to claim 1, wherein the amplification of the amplitude or the reduction in the threshold value in the at least one section is designed so that a drop in amplitude, which is brought about by damping, is due to at least one of the damping and a power loss and is compensated entirely.

19. An arrangement for ultrasonic testing, the arrangement comprising:
a phased array ultrasonic transducer including a first ultrasonic transducer element and a second ultrasonic transducer element, the phased array ultrasonic transducer configured to cause oblique sound incidence of an ultrasonic pulse transmitted by the first ultrasonic transducer element over a sound incidence surface into a test object and for receiving the echo signal from the test object by the second ultrasonic transducer element; and
an evaluation unit for evaluating the amplitude characteristic of the echo signal over time in a predefined defect expectation interval of time and for comparison of the amplitude with a predefined threshold value,
wherein the evaluation unit is also designed to amplify the amplitude characteristic of the echo signal in at least one of at least one section of the defect expectation interval of time and to lower the threshold value.

20. The arrangement according to claim 19, further comprising a test object, wherein the test object is a body having parallel walls, and one of the walls comprises the sound incidence surface.

* * * * *